(12) United States Patent
De Kraker

(10) Patent No.: US 8,383,869 B2
(45) Date of Patent: Feb. 26, 2013

(54) OLEFIN OLIGOMER COMPOSITION

(75) Inventor: Abraham Robert De Kraker, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 63 days.

(21) Appl. No.: 12/873,453

(22) Filed: Sep. 1, 2010

(65) Prior Publication Data

US 2011/0054209 A1   Mar. 3, 2011

Related U.S. Application Data

(60) Provisional application No. 61/238,792, filed on Sep. 1, 2009.

(51) Int. Cl.
*C10M 105/04* (2006.01)
*C07C 9/22* (2006.01)

(52) U.S. Cl. .............................. 585/16; 585/18; 508/110

(58) Field of Classification Search ................... 585/16, 585/18
See application file for complete search history.

(56) References Cited

U.S. PATENT DOCUMENTS

| | | | |
|---|---|---|---|
| 3,231,621 A | 1/1966 | Slaugh | 260/604 |
| 3,239,566 A | 3/1966 | Slaugh | 260/604 |
| 3,239,569 A | 3/1966 | Slaugh | 260/632 |
| 3,239,570 A | 3/1966 | Slaugh | 260/632 |
| 3,239,571 A | 3/1966 | Slaugh | 260/632 |
| 3,420,898 A | 1/1969 | Van Winkle | 260/632 |
| 3,440,291 A | 4/1969 | Van Winkle | 260/632 |
| 3,448,157 A | 6/1969 | Slaugh | 260/604 |
| 3,448,158 A | 6/1969 | Slaugh | 260/604 |
| 3,496,203 A | 2/1970 | Morris | 260/439 |
| 3,496,204 A | 2/1970 | Morris | 260/439 |
| 3,501,515 A | 3/1970 | Van Winkle | 260/439 |
| 3,527,818 A | 9/1970 | Mason | 260/632 |
| 4,045,507 A | 8/1977 | Cupples et al. | 560/683.15 B |
| 4,599,476 A | 7/1986 | Drent | 585/511 |
| 4,634,793 A | 1/1987 | Drent | 560/243 |
| 4,658,078 A | 4/1987 | Slaugh et al. | 585/512 |
| 5,113,030 A * | 5/1992 | Chen et al. | 585/10 |
| 5,157,177 A * | 10/1992 | Pelrine et al. | 585/10 |
| 5,420,372 A * | 5/1995 | Beach et al. | 585/522 |
| 5,849,972 A | 12/1998 | Vicari et al. | 585/531 |
| 6,063,973 A * | 5/2000 | Sen et al. | 585/18 |
| 6,150,576 A * | 11/2000 | Jiang et al. | 585/18 |
| 6,479,722 B1 | 11/2002 | De Wet et al. | 585/511 |
| 6,770,791 B2 | 8/2004 | Mathys et al. | 585/327 |
| 7,018,525 B2 * | 3/2006 | Miller et al. | 208/27 |
| 7,129,197 B2 | 10/2006 | Song et al. | 508/591 |
| 7,179,947 B2 * | 2/2007 | Lueken et al. | 568/451 |
| 8,129,572 B2 * | 3/2012 | Sigl et al. | 568/909 |
| 2006/0014989 A1 | 1/2006 | De Boer et al. | 585/324 |
| 2006/0173223 A1* | 8/2006 | De Weerd | 585/16 |

* cited by examiner

*Primary Examiner* — Ellen McAvoy

(57) ABSTRACT

An oligomer of alpha olefin is produced in a three step process comprising 1) oligomerization to a vinylidene, 2) hydroformylation to a primary alcohol, and 3) dimerization of the alcohol. The final product can be hydrogenated to form a branched alkane with improved lubricating oil properties.

9 Claims, 3 Drawing Sheets

GC Analysis of I, Decene Dimer from Example 1

Figure 1: GC Analysis of I, Decene Dimer from Example 1
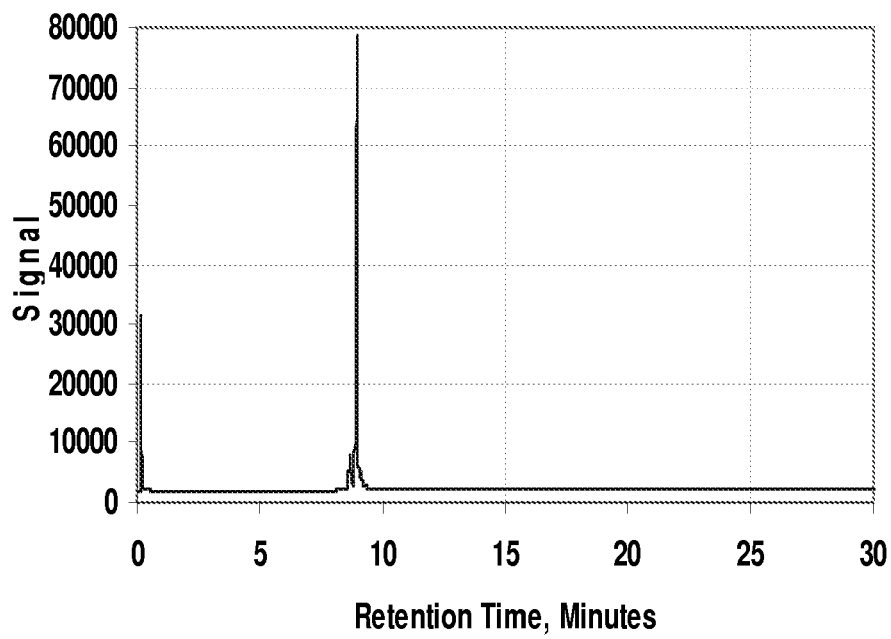
Figure 2: GC Analysis of II, Hydroformylated Decene Dimer from Example 1
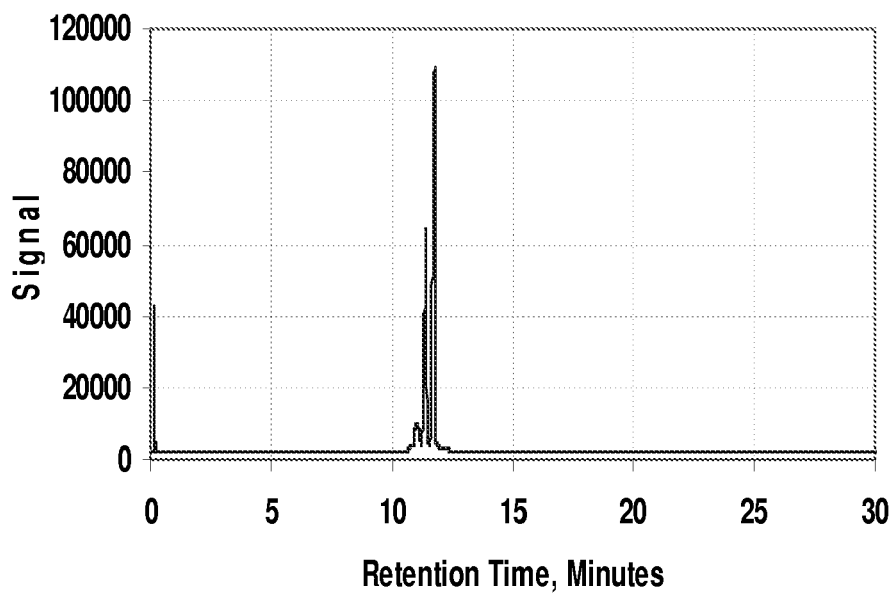

Figure 3: GC Analysis of IIIa, Dimerized Hydroformylation Product from Example 1
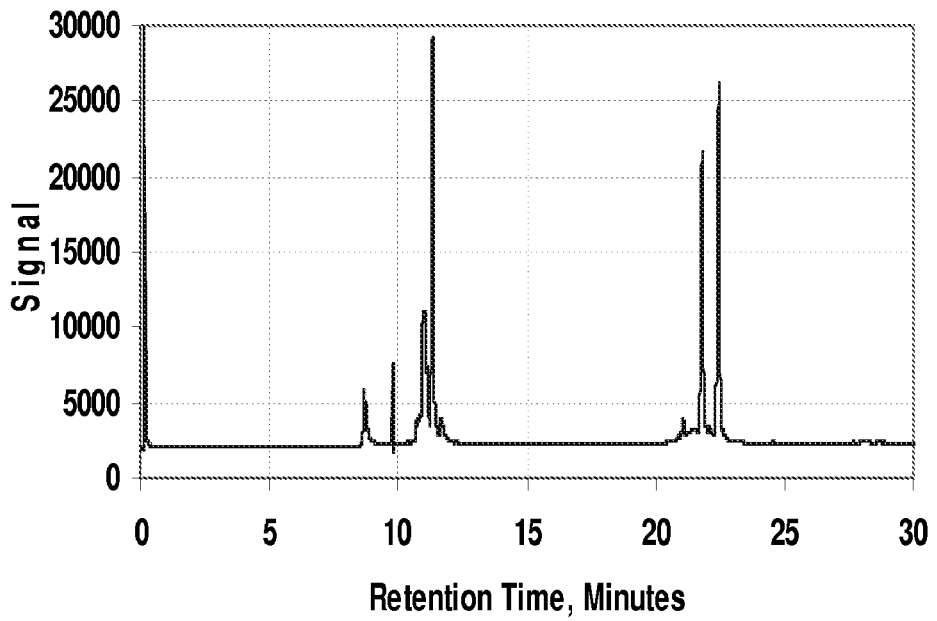
Figure 4: GC Analysis of IV, Final Product from Example 1
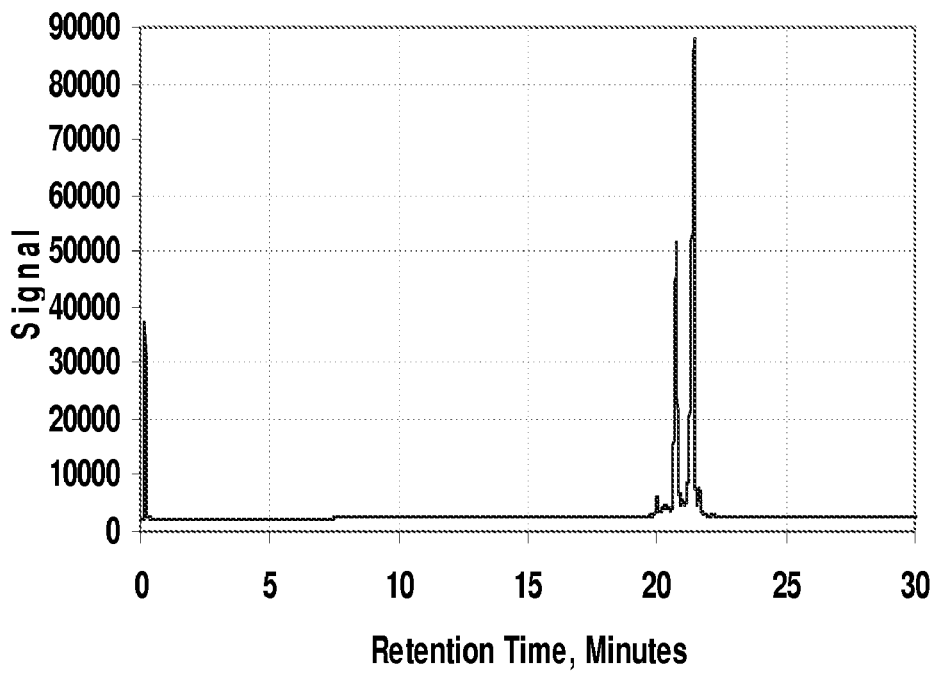

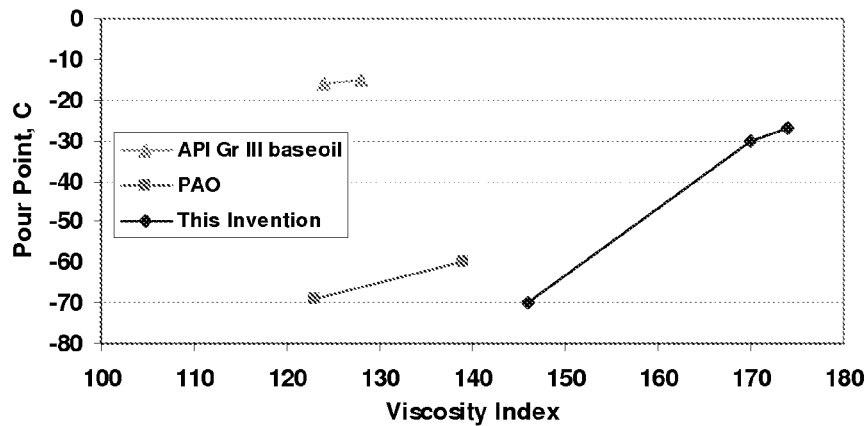
Figure 5: Viscometrics
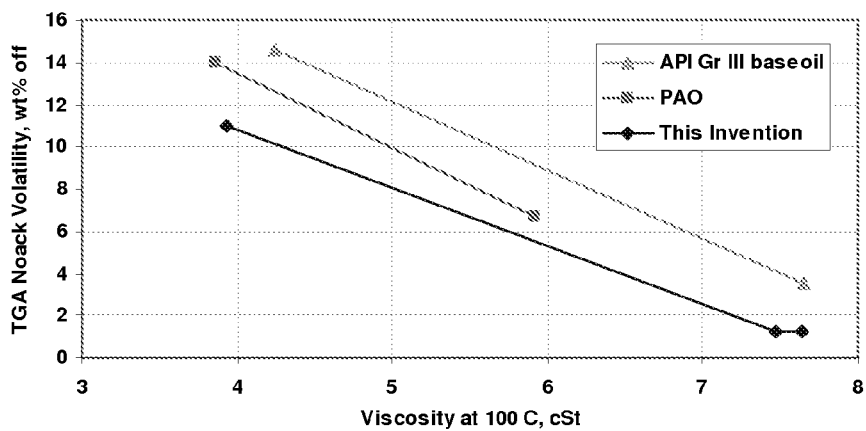
Figure 6: Volatility
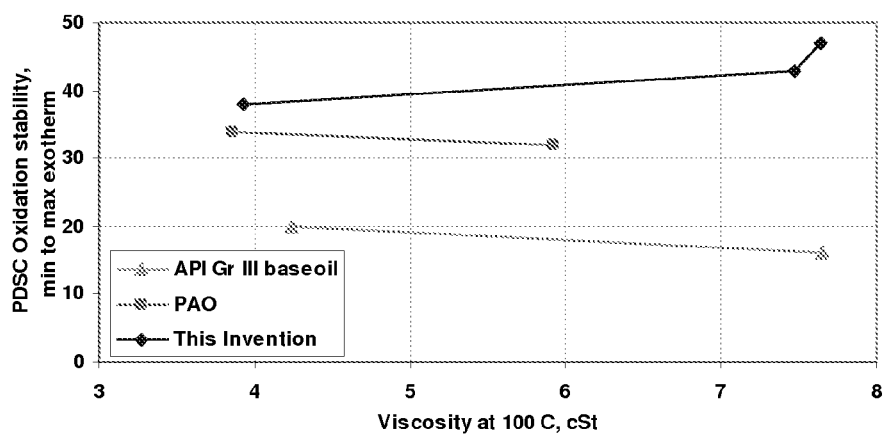
Figure 7: Oxidation Stability

OLEFIN OLIGOMER COMPOSITION

RELATED CASES

The present application claims priority from U.S. Application Ser. No. 61/238,792 filed Sep. 1, 2009, which is incorporated herein by reference.

FIELD OF THE INVENTION

The invention relates to hydrocarbon base oils that have properties particularly useful in the area of lubrication. In particular, the present invention relates to base oils having high viscosity indices, low volatility, and good oxidation stability, and to a method for making such oils.

BACKGROUND OF THE INVENTION

Poly Alpha Olefins (PAOs) are known and used as lubricating oils or in lubricating oil formulations. PAOs are typically dimers, trimers and tetramers of 1-octene, 1-decene and/or 1-dodecene and are made by a two-stage process such as that described in U.S. Pat. No. 4,045,507. Alpha olefins can also be oligomerized by metallocene catalyst, as described in U.S. Pat. No. 4,658,078 and U.S. Pat. No. 7,129,197. Other synthetic lubricating oils are esters or alkylated naphthalenes. Highly refined fractions of crude oil are also used as lubricating oils.

Each of these classes of lubricating oil have physical and chemical properties that make them useful as a lubricating oil. Nonetheless, there is still a need for lubricating oils with improved properties. This is particularly the case as the demands on lubricating oils increase.

SUMMARY OF THE INVENTION

The present invention provides a lubricating oil with a combination of physical and chemical properties that is significantly superior to the prior art. Oils in accordance with the invention may be produced in a three-step process comprising 1) oligomerization of an alpha olefin to a vinylidene, 2) hydroformylation to a primary alcohol, and 3) dimerization of the alcohol. The final product can be hydrogenated to form a branched alkane with improved properties as a lubricating base oil. Alternatively, the dimerized alcohol of step 3) above can be used to form an ester with a suitable organic acid, the ester also being useful as a lubricant.

Dimerization of the alpha olefin using metallocene catalyst results in a single vinylidene compound. Hydroformylation of the vinylidene results in three primary alcohol compounds corresponding to hydroformylation at any one of the three terminal carbons of the vinylidene. Dimerization of the alcohol mixture is preferably carried out by the Guerbet reaction, which requires a hydrogen to be present on the carbon beta to the alcohol group. This is true in all cases here, but it has been found that the beta carbon that was originally vinylidene does not react. Thus, of the nine dimers that are possible from the three alcohols, only six are actually formed. The mixture of six isomers, after hydrogenation, is found to have superior viscosity index, volatility, and oxidation stability compared to available lubricating base oils.

According to preferred embodiments, the invention comprises a mixture of structural isomers of saturated aliphatic hydrocarbon having the structural formula:

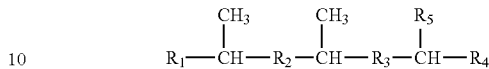

wherein $R_1$, $R_4$, and $R_5$ are the same or different, straight chain alkyl groups, $R_2$ and $R_3$ are the same or different, straight chain methylene chains, and each R group contains from 1 to 23 carbon atoms according to the following schedule:

| Isomer # | C# of the alkyl chains | | | | |
|---|---|---|---|---|---|
| | R1 | R2 | R3 | R4 | R5 |
| AA | n | n − 1 | n − 3 | n | 1 |
| AB | n | n − 1 | n − 1 | n − 2 | 1 |
| BA | n − 2 | n + 1 | n − 3 | n | 1 |
| BB | n − 2 | n + 1 | n − 1 | n − 2 | 1 |
| CA | n | n − 3 | 2 | n | n − 2 |
| CB | n − 2 | n − 1 | 2 | n | n − 2 | and the percentage of each isomer is greater than 1% and less than 95%, n being an integer from 4 to 22 which corresponds to the carbon number of the starting alpha olefin. In various embodiments, $R_1$-$R_5$ may each contain from 1 to 17 carbon atoms (n=4 to 16), from 3 to 15 carbon atoms (n=6 to 14), from 3 to 13 carbon atoms (n=6 to 12), from 5 to 13 carbon atoms (n=8 to 12), from 5 to 11 carbon atoms (n=8 to 10), or from 7 to 13 carbon atoms (n=10 to 12).

Alternative embodiments of the invention include a process for the production of aliphatic hydrocarbons, comprising: a) dimerizing an olefin of the formula alkyl-CH=$CH_2$ containing a total of 4 to 22 carbon atoms or a mixture of said olefins, the alkyl groups defined as above, in the presence of a metallocene catalyst, so as to form an olefin dimer; b) hydroformylating the olefin dimer in the presence of a hydroformylation catalyst; c) optionally, purifying the hydroformylated olefin dimer by distillation; d) dimerizing the hydroformylated olefin dimer by means of a Guerbet reaction; e) catalytically hydrogenating the product obtained in step d); and f) recovering the saturated aliphatic hydrocarbon product thus obtained. In some embodiments, the metallocene catalyst may be bis(cyclopentadienyl) zirconium dichloride. In some embodiments, the hydroformylation catalyst may be a complex of cobalt carbonyl with triphenyl phosphine ligand.

In still other embodiments, the invention is the ester formed by reacting the Guerbet alcohol with a suitable organic acid.

In still other embodiments, the invention is a lubricating oil composition comprising at least 10% of the mixture of saturated hydrocarbons as set out herein.

BRIEF DESCRIPTION OF THE FIGURES

For a more complete understanding of the invention described herein, reference will be made to the accompanying Figures, wherein:

FIGS. 1-4 are plots showing simulated GC distillations by ASTM D6417 for the intermediate and final products; and FIGS. 5-7 are plots showing various properties of the current invention as compared to known compositions.

DETAILED DESCRIPTION OF THE INVENTION

According to preferred embodiments, the present invention is a new composition of matter having the general structure:

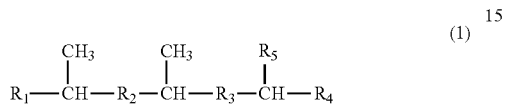
(1)

where $R_1$ through $R_5$ are alkyl or methylene chains related in a specific way, and depend on the alpha olefin used as the starting material. For a linear alpha olefin of n carbon atoms, the product will have a carbon number of 4n+2. It will consist of primarily 6 structural isomers, all with the same general structure of (1).

Compounds having the structure shown at (1) can be synthesized from linear alpha olefins of carbon number from 3 (propylene) to 20 (eicosene). A pure alpha olefin may be used, or a mixture of two or more alpha olefins can be used. If a branched alpha olefin is used, more than 6 structural isomers are possible for the final product.

The preferred first step of the synthesis is a dimerization to produce a vinylidene containing hydrocarbon:

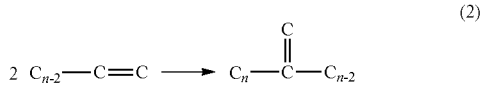
(2)

The hydrogens are omitted here for clarity. The dimerization can be carried out by any suitable method, such as the one described in U.S. Pat. No. 4,658,078, the disclosures of which are incorporated herein by reference. The product may be distilled if desired to remove unreacted monomer and any trimer or higher oligomers that may have formed, or the product may be used directly in the next step.

The dimer product (2) is preferably then converted to a primary alcohol, again by any convenient method such as the one described in U.S. Pat. No. 3,448,157, the disclosures of which are incorporated herein by reference. Conversion of olefins to primary alcohols can be accomplished, for example, by hydroformylation, by oxidation and hydrolysis, by sulfation and hydration, by epoxidation and hydration, or the like. In hydroformylation, the olefin is converted to an alkanol by reaction with carbon monoxide and hydrogen according to the Oxo process. Most commonly used is the modified Oxo process, using a phosphine, phosphite, arsine, or pyridine ligand modified cobalt or rhodium catalyst, as described in U.S. Pat. Nos. 3,231,621; 3,239,566; 3,239,569; 3,239,570; 3,239,571; 3,420,898; 3,440,291; 3,448,158; 3,448,157; 3,496,203; 3,496,204; 3,501,515; 3,527,818, the disclosures of which are incorporated herein by reference.

Hydroformylation is a term used in the art to denote the reaction of an olefin with CO and $H_2$ to produce an aldehyde/alcohol which has one more carbon atom than the reactant olefin. Frequently in the art the term hydroformylation is utilized to cover the aldehyde and the reduction to the alcohol step in total, ie, hydroformylation refers to the production of alcohols from olefins via carbonylation and an aldehyde reduction process. As used herein, hydroformylation refers to the ultimate production of alcohols.

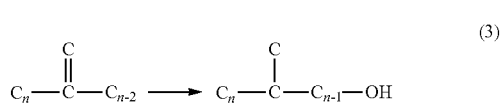
(3)

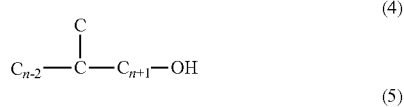
(4)

(5)

Hydroformylation adds one carbon plus an —OH group, randomly to any one of the terminal carbons in the feedstock. Thus roughly equal percentages of (3), (4), and (5) are produced. In addition, 10-20% of saturated hydrocarbon and alcohols that were hydroformylated on a carbon other than a terminal carbon are typically produced as byproducts.

In the third step of the synthesis, the mixture of (3), (4), and (5), after suitable removal of hydroformylation catalyst, unreacted olefin, and saturated hydrocarbon if desired, is subjected to a dimerization by the Guerbet reaction. This can be carried out by any of the variations of the original Guerbet reaction that have been reported in the literature, in which a primary aliphatic alcohol is converted into its β-alkylated dimer alcohol. The reaction mechanism is a four-step sequence. In the first step the alcohol is oxidized to the aldehyde. The aldehyde intermediates then react in an Aldol condensation to form vinyl aldehyde, which the hydrogenation catalyst then reduces to the alcohol.

Referring to the alcohols (3), (4), and (5) as monomers A, B, C, it was found that A and B monomers would react with themselves or each other in the Guerbet reaction. Monomer C would attack the beta carbon of either monomer A or B, but would not react with itself. Monomers A and B also did not attack the beta carbon of monomer C. Thus the possible dimers in the third step of the synthesis are: A-A, A-B, B-A, B-B, C-A, and C-B. The monomers that are not formed are: A-C, B-C, and C-C.

After hydrogenation to remove the alcohol function, all six of the dimers formed are structural isomers of the hydrocarbon $C_{4n+2}H_{8n+6}$ where n is the carbon number of the original olefin used. Referring to structure 1), the isomers will have the following specific structures, where n is the carbon number of the starting olefin:

| Isomer | C# of the alkyl chains | | | | |
|---|---|---|---|---|---|
| # | R1 | R2 | R3 | R4 | R5 |
| AA | n | n − 1 | n − 3 | n | 1 |
| AB | n | n − 1 | n − 1 | n − 2 | 1 |
| BA | n − 2 | n + 1 | n − 3 | n | 1 |
| BB | n − 2 | n + 1 | n − 1 | n − 2 | 1 |
| CA | n | n − 3 | 2 | n | n − 2 |
| CB | n − 2 | n − 1 | 2 | n | n − 2 |

The isomers will have the structures:

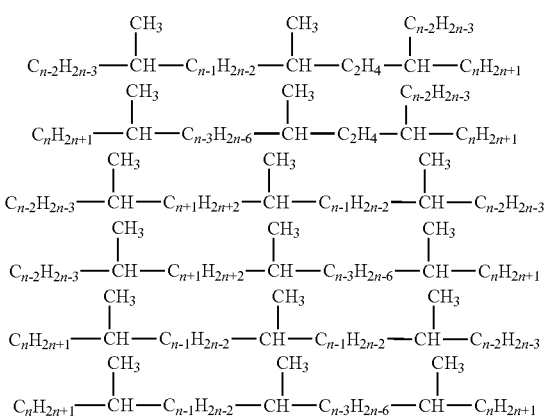

The isomers will have the structures shown below, where hydrogen has been omitted for clarity:

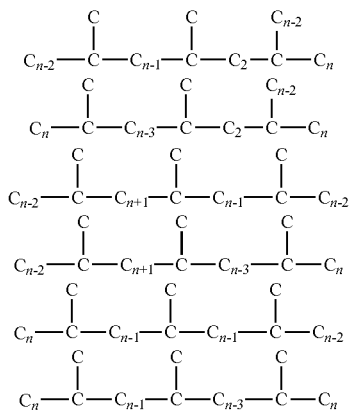

Each of the isomers formed consists of an alkyl backbone with three alkyl branches, of which at least two of the branches are methyl. The spacing of the alkyl branches divides the backbone approximately into quarters, but the exact spacing varies between each of the isomers.

EXAMPLE 1

8.4 kg of 1-decene was added to a 5 gallon reactor equipped with a cooling coil, nitrogen purge, and stirrer. The reactor was purged with nitrogen and 780 ml of 10% methylaluminoxane (MAO) in toluene was added with stirring. 168 g of 1% bis cyclopentadienyl zirconium dichloride in toluene was then added. Cooling was utilized to control the temperature at 30-35 C. After 24 hours reaction time, the batch was treated with 1.8 kg of water to convert the excess MAO to aluminum oxide. The aluminum oxide was removed by filtration and the filtrate was rotovaped to remove toluene. The rotovaped filtrate was vacuum distilled to recover 2.4 kg of decene dimer (I, 29 wt % yield based on 1-decene).

In an air-free environment, 1.5 kg of decene dimer I was combined with 67 g of phosphine modified cobalt catalyst and stirred overnight to dissolve. A 1 gallon autoclave was purged with nitrogen and the solution added. The reactor was pressurized with 2/1 ratio of $H_2$/CO to 1000 PSIG and heated to 200 C with stirring for 7 hours. The hydroformylated reactor product was vacuum distilled to recover 983 g of the hydroformylated decene dimer (II, 66 wt % yield based on I).

155 g of hydroformylated decene dimer II and 1.6 g of KOH were placed in a 3 neck flask equipped with a Dean-Stark trap, condenser, heating mantle, magnetic stirrer, and nitrogen purge. The flask was purged and then heated to 240 C with stirring for 10 hours. 2 ml of water was collected in the trap. The mixture in the flask was allowed to cool to 80 C, diluted with 200 ml Heptane, washed six times with 500 ml of hot water, dried with magnesium sulfate, and distilled to remove the Heptane (product IIIa). The product was vacuum distilled to remove unreacted hydroformylated decene dimer II, leaving 71 g of residual oil (IIIb, 46 wt % based on II).

The residual oil III was hydrotreated using a continuous fixed bed hydrotreating reactor containing Palladium on Alumina catalyst, at 2000 PSIG hydrogen pressure and 340 C. The product was recycled until IR analysis indicated complete conversion of the alcohol to water. 70 g of the hydrotreated oil was vacuum distilled to remove 2 g of light material and 2 g of heavy material to obtain the final product IV.

Simulated GC distillations by ASTM D6417 are shown in FIGS. 1-4 for the intermediate and final products.

EXAMPLE 2

The same procedure as Example 1 was followed, except that the Guerbet reaction was carried out using 50% freshly made hydroformylated decene dimer and 50% hydroformylated decene dimer recovered as unreacted material from the Guerbet reaction in Example 1. The unreacted material is essentaily depleted in monomers A and B and concentrated in monomer C. Thus in this example the concentration of monomer C is increased, leading to formation of more of dimers CA and CB in the final product. This is reflected in a shift in the physical properties as shown in Table 2. Recycle of unreacted monomer in the Guerbet reaction is a means of controlling the ratio of the isomers in the final product, thereby controlling the physical properties of the final product.

EXAMPLE 3

The same procedure as Example 1 was used, except that 1-Heptene was used as the starting material instead of 1-Decene.

EXAMPLE 4

The same procedure as Example 1 was used, except that 1-Octene was used as the starting material instead of 1-Decene.

EXAMPLE 5

The same procedure as Example 1 was used, except that decene trimer was isolated from the first step instead of decene dimer, and subjected to the same subsequent steps of hydroformylation, dimerization, and hydrogenation.

Properties of the oils produced in Examples 1-5 are shown in Table 2. Properties of prior art lubricating baseoils are shown in Table 3. The properties of the current invention are compared to prior art in FIGS. 5-7. As can be seen, the viscosity index and oxidation stability of the present invention are higher than both API Group III base oil and PAO, while volatility is lower. Hence it is expected that oils according to the present invention will be superior to both API Group III base oil and PAO for many applications.

TABLE 2

Properties of Example Oils

| Example | Kin Vis, cSt/40 C. ASTM D445 | Kin Vis, cSt/100 C. ASTM D445 | VI ASTM D2270 | Pour Point, C. ASTM D5950 | PDSC[1] Min to max 160 C. 500 PSI O2 | TGA[2] Noack Wt % off |
|---|---|---|---|---|---|---|
| 1 | 38.2 | 7.65 | 174 | −27 | 47 | 1.3 |
| 2 | 37.7 | 7.47 | 170 | −30 | 43 | 1.2 |
| 3 | 16.1 | 3.94 | 146 | <−60 | 38 | 11.0 |
| 4 | 23.9 | 5.3 | 164 | −48 | 47 | 3.8 |
| 5 | 88.5 | 13.0 | 147 | −60 | n/a | n/a |

Notes:
[1] Pressure DSC minutes to maximum exotherm, indicating relative oxidation stability
[2] Thermogravimetric Analysis correlated to Noack Volatility, ASTM D5800.

TABLE 3

Properties of Prior Art Oils

| Commercial Baseoil | Kin Vis, cSt/40 C. ASTM D445 | Kin Vis, cSt/100 C. ASTM D445 | VI ASTM D2270 | Pour Point, C. ASTM D5950 | PDSC[1] Min to max 160 C. 500 PSI O2 | TGA[2] Noack Wt % off |
|---|---|---|---|---|---|---|
| PAO 4 | 16.9 | 3.86 | 123 | −69 | 34 | 14.0 |
| PAO 6 | 31.0 | 5.92 | 139 | −60 | 32 | 6.7 |
| API GrIII | 19.5 | 4.25 | 124 | −15 | 20 | 14.6 |
| API GrIII | 47.4 | 7.65 | 128 | −15 | 16 | 3.5 |

Notes:
[1] Pressure DSC minutes to maximum exotherm, indicating relative oxidation stability
[2] Thermogravimetric Analysis correlated to Noack Volatility, ASTM D5800.

EXAMPLE 6

The product of Example 4 was formulated into a 0W20 motor oil by blending the product with a typical additive package. No VI improver or pour point depressant was necessary to meet the SAE J300 Surface Vehicle Standard specifications.

What is claimed is:

1. A mixture of structural isomers of saturated aliphatic hydrocarbon having the structural formula:

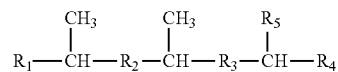

wherein $R_1$, $R_4$, and $R_5$ are the same or different alkyl groups, $R_2$ and $R_3$ are the same or different methylene chains, and each contain from 1 to 23 carbon atoms according to the following schedule:

| Isomer | C# of the alkyl chains | | | | |
|---|---|---|---|---|---|
| # | R1 | R2 | R3 | R4 | R5 |
| AA | n | n − 1 | n − 3 | n | 1 |
| AB | n | n − 1 | n − 1 | n − 2 | 1 |
| BA | n − 2 | n + 1 | n − 3 | n | 1 |
| BB | n − 2 | n + 1 | n − 1 | n − 2 | 1 |

-continued

| Isomer | C# of the alkyl chains | | | | |
|---|---|---|---|---|---|
| # | R1 | R2 | R3 | R4 | R5 |
| CA | n | n − 3 | 2 | n | n − 2 |
| CB | n − 2 | n − 1 | 2 | n | n − 2 | and the percentage of each isomer is greater than 1% and less than 95%, n being an integer from 4 to 22.

2. The mixture according to claim 1 wherein $R_1$-$R_5$ each contain from 1 to 17 carbon atoms (n=4 to 16).

3. The mixture according to claim 1 wherein $R_1$-$R_5$ each contain from 3 to 15 carbon atoms (n=6 to 14).

4. The mixture according to claim 1 wherein $R_1$-$R_5$ each contain from 3 to 13 carbon atoms (n=6 to 12).

5. The mixture according to claim 1 wherein $R_1$-$R_5$ each contain from 5 to 13 carbon atoms (n=8 to 12).

6. The mixture according to claim 1 wherein $R_1$-$R_5$ each contain from 5 to 11 carbon atoms (n=8 to 10).

7. The mixture according to claim 1 wherein $R_1$-$R_5$ each contain from 7 to 13 carbon atoms (n=10 to 12).

8. A functional fluid comprising at least 50% of the mixture of saturated hydrocarbons as defined in claim 1.

9. A functional fluid composition comprising at least 10% of the mixture of saturated hydrocarbons as defined in claim 1.

* * * * *